(12) United States Patent
Maeda et al.

(10) Patent No.: US 8,354,121 B2
(45) Date of Patent: Jan. 15, 2013

(54) TAPE PREPARATION

(75) Inventors: Hiroo Maeda, Ibaraki (JP); Naoki Ohara, Kokubunji (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 325 days.

(21) Appl. No.: 12/308,099

(22) PCT Filed: Jun. 7, 2007

(86) PCT No.: PCT/JP2007/061538
§ 371 (c)(1),
(2), (4) Date: Dec. 8, 2008

(87) PCT Pub. No.: WO2007/142295
PCT Pub. Date: Dec. 13, 2007

(65) Prior Publication Data
US 2009/0169605 A1    Jul. 2, 2009

(30) Foreign Application Priority Data

Jun. 9, 2006 (JP) .................. 2006-161072
Aug. 30, 2006 (JP) .................. 2006-232926

(51) Int. Cl.
*A61F 13/02* (2006.01)
*A61K 31/497* (2006.01)

(52) U.S. Cl. .................. 424/448; 514/253.04

(58) Field of Classification Search .............. None
See application file for complete search history.

(56) References Cited

U.S. PATENT DOCUMENTS

| | | | |
|---|---|---|---|
| 5,021,421 A | 6/1991 | Hino et al. | |
| 2002/0123490 A1* | 9/2002 | Howard, Jr. ........... | 514/220 |
| 2006/0110434 A1 | 5/2006 | Yamaguchi et al. | |
| 2007/0134310 A1* | 6/2007 | Nedberge et al. ........... | 424/449 |
| 2007/0254887 A1 | 11/2007 | Maeda et al. | |
| 2007/0269379 A1* | 11/2007 | Mitragotri et al. ........... | 424/9.2 |

FOREIGN PATENT DOCUMENTS

| | | |
|---|---|---|
| EP | 0 385 237 | 9/1990 |
| EP | 0 730 865 | 9/1996 |
| EP | 1 238 676 | 9/2002 |
| JP | 4-99768 | 3/1992 |
| WO | 96/31201 | 10/1996 |
| WO | 97/09985 | 3/1997 |
| WO | 02/053140 | 7/2002 |
| WO | 03/066039 | 8/2003 |
| WO | 2006/025516 | 3/2006 |
| WO | WO/2006/025516 * | 3/2006 |

OTHER PUBLICATIONS

English translation of PCT Written Opinion dated Jan. 22, 2009 in the International (PCT) Application PCT/JP2007/061538.
Michiaki Matsuda et al., "Determination of a novel anti-psychotic agent AD-5423 and its metabolites in plasma by high-performance liquid chromatography with fluorescence detection", Journal of Pharmaceutical and Biomedical Analysis, 15, pp. 1449-1456, 1997.
International Search Report issued Jul. 10, 2007 in the International (PCT) Application PCT/JP2007/061538.

* cited by examiner

*Primary Examiner* — Scott Long
*Assistant Examiner* — Sarah Alawadi
(74) *Attorney, Agent, or Firm* — Wenderoth, Lind & Ponack, L.L.P.

(57) ABSTRACT

It is intended to provide a preparation for percutaneous administration of 2-(4-ethyl-1-piperazinyl)-4-(4-fluoro-phenyl)-5,6,7,8,9,10-hexahydrocycloocta[b]pyridine (Compound A), which inhibits the generation of a metabolite and is capable of continuously maintaining a blood drug level. Specifically, a tape preparation comprising an adhesive layer formed on one surface of a support, characterized in that the adhesive layer contains (1) Compound A or a physiologically acceptable acid addition salt thereof, and (2) an acrylic adhesive, or (1) Compound A or a physiologically acceptable acid addition salt thereof, (2) an acrylic adhesive, and (3) a permeation enhancer is provided.

8 Claims, 1 Drawing Sheet

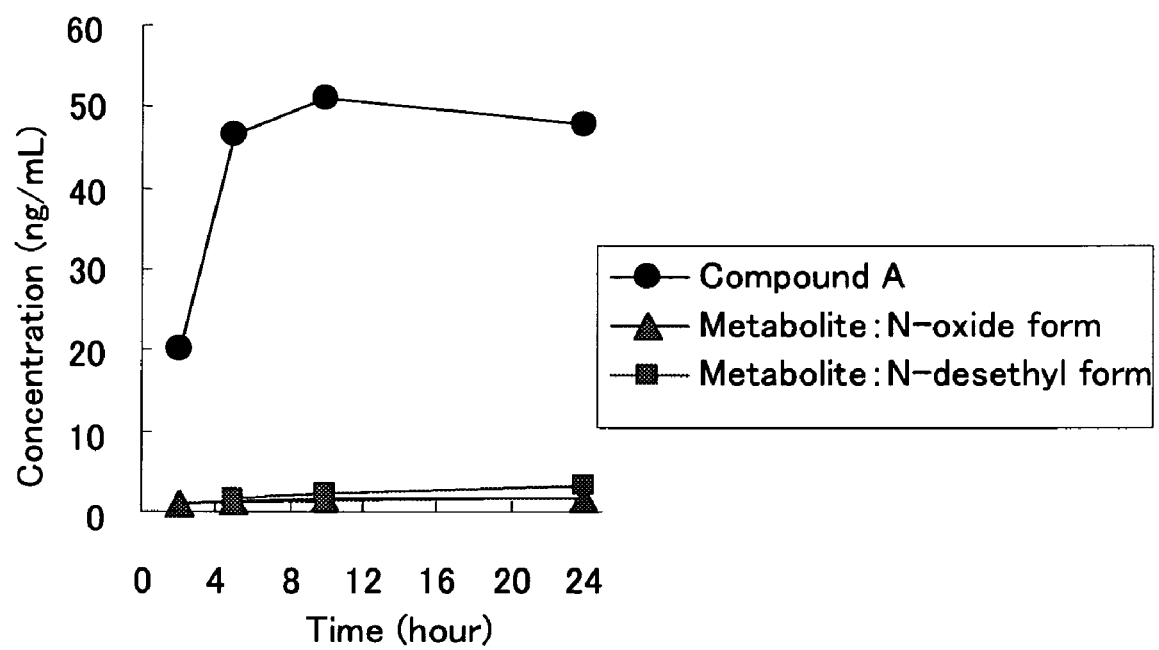

TAPE PREPARATION

TECHNICAL FIELD

The present invention relates to a tape preparation for percutaneous absorption. More particularly, it relates to a tape preparation comprising 2-(4-ethyl-1-piperazinyl)-4-(4-fluorophenyl)-5,6,7,8,9,10-hexahydrocycloocta[b]-pyridine as an active ingredient, which can continuously maintain the blood concentration of the compound when the tape preparation is put on a surface of skin.

BACKGROUND ART 2-(4-ethyl-1-piperazinyl)-4-(4-fluorophenyl)-5,6,7,8,9,10-hexahydrocycloocta[b]pyridine (hereinafter, referred to as "blonanserin"), which is a serotonin-dopamine antagonist (SDA), is disclosed in JP-B-7 (1995)-47574. Blonanserin is useful as an antipsychotic agent since it has higher affinity for dopamine D2 receptor and serotonin 5-HT2 receptor than haloperidol which is an existing antipsychotic agent.

Regarding to oral administration of blonanserin to animals, Michiaki Matsuda, et al., *J. Pharm. Biomed. Anal.*, 15, 1449-1456, 1997 (hereinafter referred to as "Reference 1") reports the time course of blood level of blonanserin and metabolites thereof, therein it is disclosed that blonanserin administered orally to animals such as a rat is metabolized to a metabolite thereof through first-pass effect.

In general, a percutaneous absorption route is known as an administration route characterized by maintaining the drug concentration in the blood more continuously than an oral administration route and by avoiding first-pass effect. In addition, a percutaneous absorption route also has an advantage that it is not affected by diet. Especially, a tape preparation which is one of transdermal administrations is useful from the viewpoint that it is easy to check out an administration and a discontinuation.

As a percutaneous absorption preparation comprising an antipsychotic agent, a transdermal formulation comprising olanzapine (WO 97/09985), a transdermal formulation comprising risperidone (WO 96/31201), and a transdermal formulation comprising perospirone (WO 2006/025516) have already been known.

In general, it is uncommon that percutaneous administration can let a sufficient amount of a medicament penetrate a skin to exert the activity of the medicament. Therefore, it is necessary to study the permeability of a medicament itself, or consider the addition of an agent that can make a skin permeation of a medicament accelerated. However, it is difficult to foresee such permeability of a medicament or the effect of such additive agent because the characteristics may easily be changed depending on the kind of a medicament. Therefore, it is thought that it impossible or very difficult to develop a percutaneous absorption formulation using a medicament useful as an oral preparation. In addition, it is also difficult to foresee if first-pass effect can be avoided via percutaneous route, from the same reason.

Therefore, it is very expectant that the above-mentioned useful antipsychotic agent: blonanserin will be developed as a percutaneous absorption formulation from the viewpoint of medical needs and pharmacokinetic effect. However, it has been thought that the development thereof is difficult because the skin permeability of blonanserin or the avoidance effect for first-pass effect via percutaneous route has not been resolved enough.

On the other hand, as some examples of a combination of an antipsychotic agent and another medicament, WO 2002/053140 discloses a composition comprising a norepinephrine reuptake inhibitor and a neuroleptic agent (antipsychotic agent), JP-A-2002-308801 discloses a composition comprising a serotonin reuptake inhibitor and an atypical antipsychotic agent, and JP-A-2006-505489 discloses a simultaneous administration of a valproate compound and an atypical antipsychotic agent, wherein in each publication blonanserin is exemplified as an antipsychotic agent, and percutaneous administration is described as one of the administration routes.

However, these publications are directed to the treatment for psychosis with a combination of 2 kinds of medicaments, blonanserin is just one example of antipsychotic agents that may be added to the combination, and further there is no example thereof. Furthermore, these publications do not describe any practical description about a composition or an effect as a percutaneous absorption preparation. After all, these publications did not disclose anything that blonanserin was applied for a percutaneous absorption preparation. Therefore, it was actually impossible to develop a percutaneous absorption preparation comprising blonanserin based on these publications.

DISCLOSURE OF INVENTION

Problems to be Solved by Invention

The present invention provides a preparation for percutaneous administration comprising blonanserin, which can inhibit the generation of a metabolite, continuously maintain the blood concentration of the drug.

Means to Solve the Problem

The present inventors have intensively studied in order to solve the above-mentioned problems, and have found that the administration of blonanserin via a tape preparation comprising an acrylic adhesive as a base material can inhibit the generation of a metabolite of blonanserin, and continuously maintain the blood concentration of blonanserin. Furthermore, the present inventors have also found that the skin permeability of blonanserin can be enhanced by using a specific permeation enhancer and the releasing amount of blonanserin from the tape preparation comprising an acrylic adhesive as a base material can be controlled, and they have accomplished the present invention.

Namely, the present invention relates to a tape preparation comprising an adhesive layer formed on one surface of a support, and provides a tape preparation characterized in that the adhesive layer comprises (1) blonanserin or a physiologically acceptable acid addition salt thereof, and (2) a polymer adhesive; or (1) blonanserin or a physiologically acceptable acid addition salt thereof, (2) a polymer adhesive, and (3) a permeation enhancer. In more detail, the present invention provides the following embodiments of the invention.

[1] A tape preparation comprising an adhesive layer formed on one surface of a support, wherein the adhesive layer comprises (1) 2-(4-ethyl-1-piperazinyl)-4-(4-fluorophenyl)-5,6,7,8,9,10-hexahydrocycloocta[b]pyridine (hereinafter referred to as "Compound A") or a physiologically acceptable acid addition salt thereof, and (2) an acrylic adhesive.

[2] A tape preparation comprising an adhesive layer formed on one surface of a support, wherein the adhesive layer comprises (1) Compound A or a physiologically acceptable acid addition salt thereof, (2) an acrylic adhesive, and (3) a permeation enhancer.

[3] The tape preparation of [1] or [2] wherein the adhesive layer comprises the ingredient (1) in a concentration of about 0.1% to about 50% by weight of Compound A.

[4] The tape preparation of any one of [1] to [3] wherein the acrylic adhesive (2) is at least one selected from the group consisting of a (co)polymer mainly containing an alkyl (meth)acrylate, and a copolymer of an alkyl (meth)acrylate and a functional monomer.

[5] The tape preparation of any one of [2] to [4] wherein the permeation enhancer (3) is at least one selected from the group consisting of a saturated or unsaturated $C_{7-22}$ aliphatic alcohol, diisopropyl adipate, medium chain fatty acid triglyceride, propylene glycol, oleic acid, crotamiton, N-methyl-2-pyrrolidone, olive oil, soybean oil, myristic acid, glycerin, macrogol 200, squalane, liquid paraffin, polyoxyethylene (160)polyoxypropylene(40)glycol, polyoxyethylene-nonylphenyl ether, lauromacrogol, a-monoisostearyl glyceryl ether, polyoxyethylene hydrogenated castor oil 10, isopropyl myristate, diethyl sebacate, sorbitan sesquioleate, polyoxyl 40 stearate, polyethylene glycol monolaurate, cetanol.polyethyleneglycol monostearate mixed wax, liquid lanolin, lactic acid, acetic acid, cetyl lactate, oleyl oleate, cetyl 2-ethylhexanoate, n-butyl acetate, l-menthol, methylisobutyl ketone and triacetin.

[6] The tape preparation of [5] wherein the permeation enhancer (3) comprises lactic acid.

[7] The tape preparation of any one of [2] to [6] wherein the adhesive layer comprises the permeation enhancer (3) in a concentration of about 0.01% to about 50' by weight.

[8] The tape preparation of any one of [1] to [7] whose target disease is schizophrenia.

[9] The tape preparation of any one of [1] to [8] wherein a surface of the adhesive layer which is the opposite side to the support is covered with a release liner.

[10] The tape preparation of any one of [1] to [9] wherein the acrylic adhesive is consisted of 2 or more kinds of acrylic adhesives.

[11] The tape preparation of any one of [1] to [10], further comprising a polymer adhesive other than an acrylic adhesive.

[12] The tape preparation of any one of [1] to [1,1] wherein the adhesive layer further comprises an antipsychotic agent other than Compound A.

Effect of the Invention

Using the tape preparation for percutaneous absorption of the present invention, it is possible to inhibit the generation of a metabolite, continuously maintain the blood concentration of blonanserin, and additionally enhance the skin permeability of blonanserin with a specific permeation enhancer.

BRIEF DESCRIPTION OF DRAWINGS

FIG. 1 shows the result following the time course of the blood concentration after administering the tape preparation of the present invention.

BEST MODE FOR CARRYING OUT THE INVENTION

The "tape preparation" herein used is synonymous with a "patch preparation".

The "adhesive layer" herein used means a layer formed on a support, which comprises a medicament.

The "% by weight" which is just described in the present claims and description means % by weight per 100% by the total weight of the adhesive layer without any solvent, which is obtained via dryness or other method.

(1) Compound A or a Physiologically Acceptable Acid Addition Salt Thereof

Compound A of the invention, i.e., 2-(4-ethyl-1-piperazinyl)-4-(4-fluorophenyl)-5,6,7,8,9,10-hexahydro-cycloocta[b]pyridine (the general name is "blonanserin") has the following chemical formula:

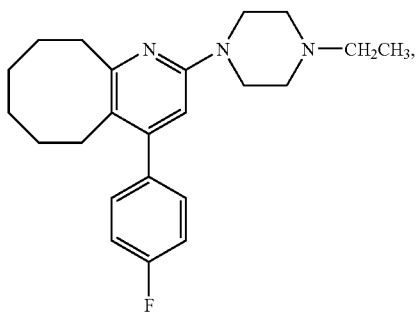

which is a serotonin-dopamine-antagonist as mentioned above, and is being developed as an antipsychotic agent.

Compound A may be formed as a free base or a physiologically acceptable acid addition salt thereof. The organic acid addition salt includes, for example, a formate, an acetate, a lactate, an adipate, a citrate, a tartrate, a methanesulfonate, a fumarate, and a maleate, and the inorganic acid addition salt includes, for example, a hydrochloride, a sulfate, a nitrate, and a phosphate, but are not limited thereto. Further, Compound A or a physiologically acceptable acid addition salt thereof may be a solvate, i.e. a hydrate or a solvate other than a hydrate.

Compound A or a physiologically acceptable acid addition salt thereof mentioned above can be prepared according to, for example, the method disclosed in JP-B-7 (1995)-47574 or a similar method thereto. The prepared Compound A or physiologically acceptable acid addition salt thereof may optionally be milled by a conventional process.

The "Compound A or physiologically acceptable acid addition salt thereof" which is comprised in the tape preparation of the present invention may be contained, per 100% by weight of the adhesive layer, generally, in about 0.1% to about 50% by weight of Compound A, preferably in about 0.1% to about 40% by weight of Compound A, and more preferably in about 0.1% to about 30% by weight of Compound A; or preferably in about 0.5% to about 50% by weight of Compound A, more preferably in about 0.5% to about 40% by weight of Compound A, and further more preferably in about 0.5% to about 30% by weight of Compound A; but it depends on the area of the tape preparation. The "by weight of Compound A" used herein means that the weight of the ingredient (1) does not contain the weight of salt acid or crystal water in case that Compound A is formed as a salt form or a hydrate form.

(2) Acrylic Adhesive

The polymer adhesive which is generally used as a base material of a tape preparation includes, for example, a silicone adhesive, a rubber adhesive, an acrylic adhesive, etc. The silicone adhesive herein includes an adhesive comprising as a main ingredient a silicone rubber such as polydimethylsiloxane and diphenylsiloxane, and the rubber adhesive herein includes, for example, natural rubber, polyisopropylene rubber, polyisobutylene, styrene-butadiene copolymer, styrene-isopropylene copolymer, styrene-isoprene-styrene block copolymer, etc.

The present invention is characterized in that it has been found that a tape preparation using especially an acrylic adhesive selected from the above-mentioned polymer adhesives can inhibit the generation of a metabolite of Compound A, and continuously maintain the blood concentration of Compound A.

The acrylic adhesive includes a (co)polymer composed of mainly alkyl (meth)acrylate; for example, a polymer composed of mainly alkyl acrylate, a polymer composed of mainly alkyl methacrylate, a copolymer composed of mainly alkyl acrylate, a copolymer composed of mainly alkyl methacrylate, an copolymer composed of mainly alkyl acrylate and alkyl methacrylate. The (co)polymer herein may be a copolymer composed of 2 or more kinds of the above-mentioned alkyl (meth)acrylate, or a copolymer composed of an alkyl (meth)acrylate and a functional monomer which can be copolymerized with an alkyl (meth)acrylate.

The "(meth)acrylate" herein means "acrylate or methacrylate", or "acrylate and/or methacrylate", and the "(co)polymer" means "polymer or copolymer", or "polymer and/or copolymer".

The alkyl (meth)acrylate denotes, for example, an alkyl (meth)acrylate which is prepared by esterifying (meth)acrylic acid with a straight or branched $C_{1-18}$ alkyl chain, and includes, for example, methyl (meth)acrylate, butyl (meth) acrylate, hexyl (meth)acrylate, octyl (meth)acrylate, nonyl (meth)acrylate, decyl (meth)acrylate, etc. The functional monomer includes, for example, a monomer having a hydroxy group (e.g. hydroxyethyl (meth)acrylate), a monomer having a carboxyl group (e.g. butyl maleate, and crotonic acid), a monomer having an amide group (e.g. (meth)acrylamide), a monomer having an amino group (e.g. dimethyl aminoacrylate), a monomer having a pyrrolidone ring (e.g. N-vinyl-2-pyrrolidone), etc.

The acrylic adhesive of the present invention may be either a single adhesive or a combination of 2 or more adhesives. In addition, it may be a mixture with another adhesive. The "another adhesive" includes, for example, a silicone adhesive, a rubber adhesive, etc.

Examples of the acrylic adhesive include, but are not limited to, a commercially available "POLYTHICK 410-SA" of Sanyo Chemical Industries, Ltd., "Oribain BPS-4849-40" of TOYO INK, "DURO-TAK 87-2194" and "DURO-TAK 387-2516" of National Starch and Chemical Co., etc.

The amount of the acrylic adhesive to be added is the rest of the adhesive layer from which Compound A or a physiologically acceptable acid addition salt thereof, the following permeation enhancer, and each of optional additive ingredients for formulation are subtracted, which is an indispensable amount to complete the adhesive layer. For example, when the adhesive layer comprises Compound A in 10% by weight and a permeation enhancer in 10% by weight, the content of an acrylic adhesive is about 80% by weight.

The adherence property of the acrylic adhesive herein means an adhesive intense just enough to be used as a pharmaceutical tape preparation, i.e. it intends that it is easily put on a skin, and it is no problem to remove it. Additionally, it is possible to optionally add a curing agent thereto, in order to provide an appropriate adhesion property for a skin. The curing agent herein includes, for example, a commercially available "POLYTHICK SC-75" of Sanyo Chemical Industries, Ltd., "BHS8515" of TOYO INK, etc. The amount of the curing agent to be added just has to be chosen so as to adapt to the property of the adhesive, for example, about 0.001 part to about 0.05 part by weight per 1 part by weight of the adhesive.

(3) Permeation Enhancer

In the present invention, it has been found that adding a specific permeation enhancer to the above-mentioned acrylic adhesive can further enhance the skin permeability of Compound A.

The preferable permeation enhancer herein used includes, but are not limited to, a saturated or unsaturated $C_{7-22}$ aliphatic alcohol such as oleyl alcohol, lauryl alcohol and decanol, diisopropyl adipate, medium chain fatty acid triglyceride, propylene glycol, oleic acid, crotamiton, N-methyl-2-pyrrolidone (NMP), olive oil, soybean oil, myristic acid, glycerin, macrogol 200, squalane, liquid paraffin, polyoxyethylene(160)polyoxy-propylene(40)glycol, polyoxyethylene-nonylphenyl ether, lauromacrogol, a-monoisostearyl glyceryl ether, polyoxy-ethylene hydrogenated castor oil 10, isopropyl myristate, diethyl sebacate, sorbitan sesquioleate, polyoxyl 40 stearate, polyethylene glycol monolaurate, cetanol.polyethyleneglycol monostearate mixed wax, liquid lanolin, lactic acid, acetic acid, cetyl lactate, oleyl oleate, cetyl 2-ethylhexanoate, n-butyl acetate, l-menthol, methylisobutyl ketone, triacetin, etc. and especially the preferable is lactic acid.

The permeation enhancer of the present invention may be either a single or a combination of 2 or more permeation enhancers, and especially a permeation enhancer comprising lactic acid is preferable. The permeation enhancer which is comprised in the tape preparation of the present invention is contained, per 100% by weight of the adhesive layer, generally, in about 0.01% to about 50% by weight, preferably in about 0.1% to about 40% by weight, and more preferably in about 0.3% to about 40% by weight.

Adhesive Layer

The adhesive layer of the present tape preparation may contain a pharmaceutically acceptable ingredient for pharmaceutical preparation which is ordinarily used for preparing a tape preparation as long as there is no particular inconvenience. As to such ingredient for pharmaceutical preparation, any ingredients which give no bad effect on the preparation and have a necessity to be formulated are available, which include, for example, a stabilizing agent, a tackifier, a plasticizer, a flavor, a filler, etc.

In addition, any active pharmaceutical ingredient other than Compound A may be comprised in the adhesive layer, which include, for example, an antipsychotic agent such as haloperidol, clozapine, risperidone, olanzapine, quetiapine, ziprasidone and aripiprazole.

The stabilizing agent herein includes, but is not limited to, for example, ascorbic acid, sodium alginate, propylene glycol alginate, dibutylhydroxytoluene, butylhydroxyanisole, tocopherol acetate, tocopherol, propyl gallate, ethyl parahydroxybenzoate, butyl parahydroxy-benzoate, propyl parahydroxybenzoate, methyl parahydroxy-benzoate, 2-mercaptobenzimidazole, etc.

The tackifier herein includes, but is not limited to, for example, ester gum, glycerin, hydrogenated rosin glycerol ester, petroleum resin, rosin, polybutene, etc. The plasticizer herein includes, but is not limited to, for example, polybutene, liquid paraffin, glycerin, glycerol esters of fatty acids, etc. The flavor herein includes, but is not limited to, for example, dl-menthol, orange oil, Mentha oil, lemon oil, rose oil, etc. The filler herein includes, but is not limited to, for example, titanium oxide, zinc oxide, starch grafted acrylate 100, etc.

Tape Preparation of the Present Invention

The tape preparation of the present invention has the above-mentioned adhesive layer formed on one side (surface) of a support and optionally has a release liner covered on the surface of the adhesive layer, which is the opposite side to the support. At the time of using the tape preparation, the release liner is released, and the adhesive layer of the tape preparation is put on a skin for percutaneous administration.

The support of the tape preparation is not particularly limited as long as a medicament is not or hardly penetrable to the stuff thereof and there is not or little influence on the release of a medicament, and either elasticized support or unelasticized one is acceptable. The support includes, but is not limited to, for example, a resin film such as ethyl cellulose, nylon, polyethylene terephthalate (PET), polyester, polypropylene, etc. or a combination thereof. And a nonwoven cloth such as PET may be covered on the side where the adhesive layer is not formed.

The surface of the support where the adhesive layer is formed can be preferably treated with, for example, corona discharge, plasma, oxidation, hairline processing, sandmat processing.

The tape preparation of the present invention can be prepared by a conventional process. For example, it can be prepared according to "Manual for the development of transdermal formulation" produced under the supervision of Mitsuo Matsumoto (1985, see the section of the preparation of plaster formulation). The plaster formulation described in the text means the same as the tape preparation defined herein.

For example, the present tape preparation can be prepared as follows: a mixture solution of Compound A or an acid addition salt thereof, and an acrylic adhesive; an optional ingredient for formulation such as a permeation enhancer and a curing agent; and an organic solvent are mixed to prepare an adhesive layer mixture. The mixture is put on one surface of a support or a release liner, which is dried to remove the organic solvent to prepare an adhesive layer. And a release liner or a support is put on the opposite side of the adhesive layer before/after the drying.

The thickness of the given adhesive layer is about 10 μm to about 400 μm, and preferably about 20 μm to about 200 μm. However, the thickness of the adhesive layer is not limited to the above-mentioned range, i.e. more or less of the range is also intended to be within the range of the present invention.

The release liner covered on the surface of the adhesive layer may be selected from a variety of materials, which has a release layer having a stripping performance on its surface, and includes, for example, a paper liner, plastic film, etc. which is treated with silicone resin or other treatment, but is not limited thereto.

The tape preparation of the present invention can be prepared in the above-mentioned manner so as to adjust the size thereof suitable for the desired dose, or can be cut to be adapted for the desired size/form.

The tape preparation may be larger than the desired size which is actually used for patients, or may be smaller than it. It this case, it is possible to optionally cut the tape preparation or put the appropriate number of the tape preparations on a skin when the tape preparation is administered. The body site to be put on includes, but is not limited to, for example, arm, shoulder, neck, back, waist, abdomen, chest, hip, leg, etc. The tape preparation of the present invention may be packed with a leaflet wherein an information of the tape preparation is described, and set in the market. The leaflet may be described on a package or may be included in a package as a package insert. The "information of the tape preparation" herein includes, for example, an information such as "it can be used for treating schizophrenia", and "it should be used for treating schizophrenia".

EXAMPLE

Hereinafter, the present invention is further illustrated by Examples, Comparative Examples, Experiments, etc., but should not be construed to be limited thereto. The "%" described in the following Examples and so on means "% by weight", unless otherwise indicated.

As a support of the invention, polyethylene terephthalate film having a thickness of 25 μm (made by FUJIMORi KOGYO CO., LTD.) was used herein. As a release liner, Bynasheet 64S-018B (made by FUJIMORi KOGYO CO., LTD.) was used herein.

Example 1

A Tape Preparation of the Present Invention 22.018 g of an acrylic adhesive (POLYTHICK 410-SA, Sanyo Chemical Industries, Ltd. (residue on evaporation: 38% by weight)), 0.044 g of a curing agent (POLYTHICK SC-75, Sanyo Chemical Industries, Ltd. (residue on evaporation: 75% by weight)) and 6 ml of ethyl acetate were mixed. To the mixture, Compound A was added so that the adhesive layer should contain Compound A in a concentration of 16%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Experiment 1

Experiment of Percutaneous Absorption

Six-week-aged SD male rat was anesthetized, and the back thereof was epilated. The tape preparation of Example 1 which had a 5 cm×5 cm square was administered to the epilated back of the rat, and the blood was chronologically collected and divided into serum. The serum was assayed with LC/MS/MS, and thereby the concentrations in the serum of Compound A and the following N-oxide form and N-desethyl form which are metabolites thereof were chronologically measured. The results are shown in FIG. 1. It was found that the administered amount was about 6.5 mg/kg by assaying the residual amount of Compound A in the tape preparation after use.

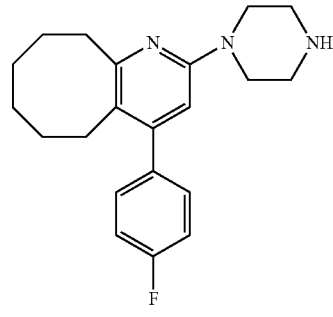

N-desethyl form

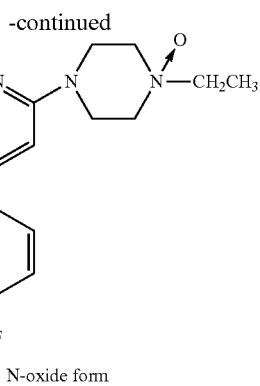

N-oxide form

The course of blood level of Compound A and N-oxide form and N-desethyl form which are metabolites thereof in the case that Compound A was orally administered to a rat has already been reported (Reference 1). According to FIG. 5 in the document, the ratio of each metabolite (around in $C_{max}$) against Compound A (3 mg/kg, p.o.) is calculated as about 0.40 in the N-oxide form and about 0.10 in the N-desethyl form.

From the blood concentration of Compound A in 10 hours after the administration in Example 1 which was around in the maximum of the blood concentration thereof, it has been found that the ratio of each metabolite against Compound A was 0.029 in the N-oxide form and 0.043 in the N-desethyl form (see FIG. 1). From this result, it has been found that the percutaneous administration of Compound A via the tape preparation of the present invention can make the production of the both metabolites markedly reduce compared with oral administration. The result indicates that the present tape preparation has an activity for markedly inhibiting the production of metabolites (markedly avoiding first-pass effect), compared with oral administration.

TABLE 1

|  | Oral administration (Reference 1) | Present invention Tape preparation of Example 1 |
|---|---|---|
| N-Oxide form/ Compound A | 0.40 | 0.029 |
| N-Desethyl form/ Compound A | 0.10 | 0.043 |

Example 2

4.77 g of an acrylic adhesive (POLYTHICK 410-SA, Sanyo Chemical Industries, Ltd.), 10.0 mg of a curing agent (POLYTHICK SC-75, Sanyo Chemical Industries, Ltd.) and 1.2 ml of ethyl acetate were mixed. To the mixture, Compound A was added so that the adhesive layer should contain Compound A in 9%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 3

4.48 g of an acrylic adhesive (Oribain BPS-4849-40, TOYO INK (residue on evaporation: 40% by weight)), 0.16 g of a curing agent (Oribain BHS-8515, TOYO INK (residue on evaporation: 30% by weight)) and 1.2 ml of ethyl acetate were mixed. To the mixture, Compound A was added so that the adhesive layer should contain Compound A in 9%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 4

4.04 g of an acrylic adhesive (DURO-TAK 87-2194, National Starch and Chemical Co. (residue on evaporation: 45% by weight)) and 1.2 ml of ethyl acetate were mixed. To the mixture, Compound A was added so that the adhesive layer should contain Compound A in 9%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 5

4.39 g of an acrylic adhesive (DURO-TAK 387-2516, National Starch and Chemical Co. (residue on evaporation: 41.5% by weight)) and 1.2 ml of ethyl acetate were mixed. To the mixture, Compound A was added so that the adhesive layer should contain Compound A in 9%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Comparative Example 1

0.50 g of styrene-isoprene-styrene block copolymer (QUINTAC 3421, ZEON CORPORATION), 0.42 g of liquid paraffin, 0.40 g of polybutene (HV-300, NIPPON OIL CORPORATION), 0.50 g of alicyclic saturated hydrocarbon resin (ARKON P-100, ARAKAWA CHEMICAL INDUSTRIES, LTD.) and 3.0 ml of ethyl acetate was added so that the adhesive layer should contain Compound A in 9%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Comparative Example 2

0.50 g of polyisobutylene (Oppanol B-100, BASF), 0.42 g of liquid paraffin, 0.40 g of polybutene (HV-300, NIPPON OIL CORPORATION), 0.50 g of alicyclic saturated hydrocarbon resin (ARKON P-100, ARAKAWA CHEMICAL INDUSTRIES, LTD.) and 10 ml of hexane were mixed. To the mixture, Compound A was added so that the adhesive layer should contain Compound A in 9%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Experiment 2

Experiment of Skin Permeability in Rat

Using abdominal skin of 6-week-aged hairless rat, each skin permeability of the tape preparations of Examples 2 to 5 and Comparative Examples 1 to 2. Namely, skin of a hairless rat was set to a horizontal in vitro diffusion cell having a penetrable area of 1.33 cm$^2$, and the receiver side was charged with 3 ml of a mixture of polyethylene glycol 200 (macrogol 200) and phosphate buffer solution (2:1), while each preparation was put on the donor side (n=4). The receiver solution was heated at 37° C., and stirred with a stirrer. 24 hours after beginning the experiment, Compound A in the receiver solution was assayed with a high-performance liquid chromatography (column: YMC A312 ODS 5 μm (6 mmf×150 mm; YMC), mobile phase: 0.01 mol/l sodium dodecylsulfate solution in water (pH 2.4 adjusted with phosphoric acid):acetonitrile:methanol (2:5:3), column temperature: 40° C., flow rate: 1.0 ml/min) to measure the permeated amount of each preparation. The results were shown in Table 2.

TABLE 2

Permeated amount of Compound A in 24 hour permeability experiment

| Example/Comparative Example | Adhesive | (μg/cm$^2$/24 hours) |
|---|---|---|
| Example 2 | an acrylic adhesive | 0.280 |
| Example 3 | an acrylic adhesive | 0.214 |
| Example 4 | an acrylic adhesive | 0.276 |
| Example 5 | an acrylic adhesive | 0.250 |
| Comparative Example 1 | styrene-isoprene-styrene block copolymer | 0.115 |
| Comparative Example 2 | polyisobutylene | 0.162 |

All the tape preparations (Examples 2 to 5) which comprised an acrylic adhesive exhibited an excellent skin permeability, compared with the preparations comprising a rubber adhesive (styrene-isoprene-styrene block copolymer (Comparative Example 1) and polyisobutylene (Comparative Example 2).

Example 6

4.25 g of an acrylic adhesive (POLYTHICK 410-SA, Sanyo Chemical Industries, Ltd.), 9.0 mg of a curing agent (POLYTHICK SC-75, Sanyo Chemical Industries, Ltd.) and 1.2 ml of ethyl acetate were added to a vessel. Oleyl alcohol as a permeation enhancer was also added thereto so that the adhesive layer should contain oleyl alcohol in 10%, and the mixture was mixed. To the mixture, Compound A was added so that the adhesive layer should contain Compound A in 9%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Examples 7 to 42

The tape preparations shown in Table 3 were prepared by using a variety of permeation enhancers shown in Table 3 instead of oleyl alcohol in Example 6.

TABLE 3

| | Permeation enhancer (Content in adhesive layer: % by weight) |
|---|---|
| Example 7 | lauryl alcohol (10) |
| Example 8 | decanol (10) |
| Example 9 | diisopropyl adipate (10) |
| Example 10 | medium chain fatty acid triglyceride (10) |
| Example 11 | propylene glycol (10) |
| Example 12 | oleic acid (10) |
| Example 13 | crotamiton (10) |
| Example 14 | N-methyl-2-pyrrolidone (NMP) (10) |
| Example 15 | olive oil (10) |
| Example 16 | soybean oil (10) |
| Example 17 | myristic acid (10) |
| Example 18 | glycerin (10) |
| Example 19 | macrogol 200 (10) |
| Example 20 | squalane (10) |
| Example 21 | liquid paraffin (10) |
| Example 22 | polyoxyethylene(160)polyoxypropylene(40)glycol (10) |
| Example 23 | polyoxyethylene-nonylphenyl ether (10) |
| Example 24 | lauromacrogol (10) |
| Example 25 | a-monoisostearyl glyceryl ether (10) |
| Example 26 | polyoxyethylene hydrogenated castor oil 10 (10) |
| Example 27 | isopropyl myristate (10) |
| Example 28 | diethyl sebacate (10) |
| Example 29 | sorbitan sesquioleate (10) |
| Example 30 | polyoxyl 40 stearate (10) |
| Example 31 | polyethylene glycol monolaurate (10) |
| Example 32 | cetanol•polyethyleneglycol monostearate mixed wax (10) |
| Example 33 | liquid lanolin (10) |
| Example 34 | lactic acid (10) |
| Example 35 | acetic acid (10) |
| Example 36 | cetyl lactate (10) |
| Example 37 | oleyl oleate (10) |
| Example 38 | cetyl 2-ethylhexanoate (10) |
| Example 39 | n-butyl acetate (10) |
| Example 40 | 1-menthol (10) |
| Example 41 | methylisobutyl ketone (10) |
| Example 42 | triacetin (10) |

Example 43

3.72 g of an acrylic adhesive (POLYTHICK 410-SA, Sanyo Chemical Industries, Ltd.), 7.0 mg of a curing agent (POLYTHICK SC-75, Sanyo Chemical Industries, Ltd.) and 1.2 ml of ethyl acetate were added to a vessel. Oleyl alcohol and N-methyl-2-pyrrolidone were also added thereto so that the adhesive layer should contain oleyl alcohol in 10% and N-methyl-2-pyrrolidone in 10%, and the mixture was mixed. To the mixture, Compound A was added so that the adhesive layer should contain Compound A in 9%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 44

4.72 g of an acrylic adhesive (POLYTHICK 410-SA, Sanyo Chemical Industries, Ltd.), 9.0 mg of a curing agent (POLYTHICK SC-75, Sanyo Chemical Industries, Ltd.) and 1.2 ml of ethyl acetate were added to a vessel. Lactic acid was also added thereto so that the adhesive layer should contain lactic acid in 1%, and the mixture was mixed. To the mixture, Compound A was added so that the adhesive layer should contain Compound A in 9%, and the given mixture was stirred well. The mixture was flatly laid on a support so that the thickness of the adhesive layer after dried should be about 50

μm. And then it was dried at room temperature for a week. Then, a release liner was laminated on the opposite side of the adhesive layer to the support to prepare a tape preparation.

Example 45

4.51 g of an acrylic adhesive (POLYTHICK 410-SA, Sanyo Chemical Industries, Ltd.), 9.0 mg of a curing agent (POLYTHICK SC-75, Sanyo Chemical Industries, Ltd.) and 1.2 ml of ethyl acetate were added to a vessel. Lactic acid was also added thereto so that the adhesive layer should contain lactic acid in 5%, and the mixture was mixed. To the mixture, Compound A was added so that the adhesive layer should contain Compound A in 9%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 46

3.88 g of an acrylic adhesive (POLYTHICK 410-SA, Sanyo Chemical Industries, Ltd.), 8.0 mg of a curing agent (POLYTHICK SC-75, Sanyo Chemical Industries, Ltd.) and 1.2 ml of ethyl acetate were added to a vessel. Lactic acid was also added thereto so that the adhesive layer should contain lactic acid in 10%, and the mixture was mixed. To the mixture, Compound A was added so that the adhesive layer should contain Compound A in 16%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Reference Example 1

To 90 mg of Compound A was added phosphate buffer solution (pH 7.2) so that the concentration of Compound A should be 18% by weight, to give a mixture thereof.

Experiment 3

Using the same manner as Experiment 2, each skin permeability of the tape preparations of Examples 6 to 46 and the mixture of Reference Example 1 was tested. The results were shown in Table 4.

TABLE 4

| Permeated amount of Compound A in 24 hour permeability experiment | | | |
|---|---|---|---|
| Reference Example/Example (Permeation enhancer) | ($\mu g/cm^2/24$ hours) | Comparative Example/Example (Permeation enhancer) | ($\mu g/cm^2/24$ hours) |
| Reference Example 1 | 0.082 | Example 26 (polyoxyethylene hydrogenated castor oil 10) | 0.477 |
| Example 6 (oleyl alcohol) | 0.601 | Example 27 (isopropyl myristate) | 0.578 |
| Example 7 (lauryl alcohol) | 0.603 | Example 28 (diethyl sebacate) | 0.432 |
| Example 8 (decanol) | 0.370 | Example 29 (sorbitan sesquioleate) | 0.445 |
| Example 9 (diisopropyl adipate) | 0.504 | Example 30 (polyoxyl 40 stearate) | 0.420 |
| Example 10 (medium chain fatty acid triglyceride) | 0.367 | Example 31 (polyethylene glycol monolaurate) | 0.436 |
| Example 11 (propylene glycol) | 0.537 | Example 32 (cetanol•polyethyleneglycol monostearate mixed wax) | 0.480 |
| Example 12 (oleic acid) | 0.427 | Example 33 (liquid lanolin) | 0.400 |
| Example 13 (crotamiton) | 1.218 | Example 34 (lactic acid) | 8.100 |
| Example 14 (N-methyl-2-pyrrolidone) | 0.406 | Example 35 (acetic acid) | 0.588 |
| Example 15 (olive oil) | 0.931 | Example 36 (cetyl lactate) | 0.574 |
| Example 16 (soybean oil) | 0.560 | Example 37 (oleyl oleate) | 0.565 |
| Example 17 (myristic acid) | 0.446 | Example 38 (cetyl 2-ethylhexanoate) | 0.345 |
| Example 18 (glycerin) | 0.455 | Example 39 (n-butyl acetate) | 0.408 |
| Example 19 (macrogol 200) | 0.290 | Example 40 (1-menthol) | 0.886 |
| Example 20 (squalane) | 0.386 | Example 41 (methylisobutyl ketone) | 0.289 |
| Example 21 (liquid paraffin) | 0.296 | Example 42 (triacetin) | 0.379 |
| Example 22 (polyoxyethylene(160)-polyoxypropylene (40) glycol) | 0.412 | Example 43 (Oleyl alcohol + NMP) | 0.696 |
| Example 23 (polyoxyethylene-nonylphenyl ether) | 0.406 | Example 44 (lactic acid 1%) | 0.734 |
| Example 24 (lauromacrogol) | 0.545 | Example 45 (lactic acid 5%) | 1.396 |
| Example 25 (α-monoisostearyl glyceryl ether) | 0.522 | Example 46 (lactic acid 10% + Compound A 16%) | 3.121 |

All the tape preparations shown in Table 4 which comprised a specific permeation enhancer in each Example exhibited an excellent skin permeability compared with the tape preparation of Example 2 which was prepared in the same manner besides missing a permeation enhancer (see, Table 2, the permeated amount: 0.280 $\mu g/cm^2/24$ hours) Especially using lactic acid as a permeation enhancer, it was exhibited that the skin permeability of Compound A was markedly enhanced. Hereinafter, an effect which the amounts of Compound A and the permeation enhancer affect the permeability and so on were studied using lactic acid as a permeation enhancer.

Example 47

4.46 g of an acrylic adhesive (POLYTHICK 410-SA, Sanyo Chemical Industries, Ltd.), 9.0 mg of a curing agent (POLYTHICK SC-75, Sanyo Chemical Industries, Ltd.) and 1.2 ml of ethyl acetate were added to a vessel. Lactic acid was also added thereto so that the adhesive layer should contain lactic acid in 10%, and the mixture was mixed. To the mixture, Compound A was added so that the adhesive layer should contain Compound A in 5%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 48

4.19 g of an acrylic adhesive (POLYTHICK 410-SA, Sanyo Chemical Industries, Ltd.), 8.0 mg of a curing agent (POLYTHICK SC-75, Sanyo Chemical Industries, Ltd.) and 1.2 ml of ethyl acetate were added to a vessel. Lactic acid was also added thereto so that the adhesive layer should contain lactic acid in 10%, and the mixture was mixed. To the mixture, Compound A was added so that the adhesive layer should contain Compound A in 10%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 49

3.67 g of an acrylic adhesive (POLYTHICK 410-SA, Sanyo Chemical Industries, Ltd.), 7.0 mg of a curing agent (POLYTHICK SC-75, Sanyo Chemical Industries, Ltd.) and 1.2 ml of ethyl acetate were added to a vessel. Lactic acid was also added thereto so that the adhesive layer should contain lactic acid in 10%, and the mixture was mixed. To the mixture, Compound A was added so that the adhesive layer should contain Compound A in 20%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 50

3.15 g of an acrylic adhesive (POLYTHICK 410-SA, Sanyo Chemical Industries, Ltd.), 6.0 mg of a curing agent (POLYTHICK SC-75, Sanyo Chemical Industries, Ltd.) and 1.2 ml of ethyl acetate were added to a vessel. Lactic acid was also added thereto so that the adhesive layer should contain lactic acid in 10%, and the mixture was mixed. To the mixture, Compound. A was added so that the adhesive layer should contain Compound A in 30%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 51

2.62 g of an acrylic adhesive (POLYTHICK 410-SA, Sanyo Chemical Industries, Ltd.), 5.0 mg of a curing agent (POLYTHICK SC-75, Sanyo Chemical Industries, Ltd.) and 1.2 ml of ethyl acetate were added to a vessel. Lactic acid was also added thereto so that the adhesive layer should contain lactic acid in 10%, and the mixture was mixed. To the mixture, Compound A was added so that the adhesive layer should contain Compound A in 40%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 52

2.10 g of an acrylic adhesive (POLYTHICK 410-SA, Sanyo Chemical Industries, Ltd.), 4.0 mg of a curing agent (POLYTHICK SC-75, Sanyo Chemical Industries, Ltd.) and 1.2 ml of ethyl acetate were added to a vessel. Lactic acid was also added thereto so that the adhesive layer should contain lactic acid in 10%, and the mixture was mixed. To the mixture, Compound A was added so that the adhesive layer should contain Compound A in 50%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Experiment 4

Using the same manner as Experiment 2, each skin permeability of the formulations of Examples 47 to 52 was tested. The results were shown in Table 5.

TABLE 5

| Permeated amount of Compound A in 24 hour permeability experiment | |
|---|---|
| Example (Concentration of Compound A) | ($\mu g/cm^2$/24 hours) |
| Example 47 (5%) | 2.547 |
| Example 48 (10%) | 4.341 |
| Example 49 (20%) | 6.108 |
| Example 50 (30%) | 5.512 |
| Example 51 (40%) | 5.729 |
| Example 52 (50%) | 5.325 |

All the tape preparations prepared in each Example wherein the content of Compound A is 5% to 50% exhibited an excellent skin permeability, and the high permeation enhancing property was maintained with a permeation enhancer.

Example 53

4.70 g of an acrylic adhesive (POLYTHICK 410-SA, Sanyo Chemical Industries, Ltd.), 9.0 mg of a curing agent (POLYTHICK SC-75, Sanyo Chemical Industries, Ltd.) and 1.2 ml of ethyl acetate were added to a vessel. Lactic acid was also added thereto so that the adhesive layer should contain lactic acid in 0.3%, and the mixture was mixed. To the mixture, Compound A was added so that the adhesive layer should contain Compound A in 10%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 54

4.70 g of an acrylic adhesive (POLYTHICK 410-SA, Sanyo Chemical. Industries, Ltd.), 9.0 mg of a curing agent (POLYTHICK SC-75, Sanyo Chemical Industries, Ltd.) and 1.2 ml of ethyl acetate were added to a vessel. Lactic acid was also added thereto so that the adhesive layer should contain lactic acid in 0.5%, and the mixture was mixed. To the mixture, Compound A was added so that the adhesive layer should contain Compound A in 10%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 55

4.46 g of an acrylic adhesive (POLYTHICK 410-SA, Sanyo Chemical Industries, Ltd.), 9.0 mg of a curing agent (POLYTHICK SC-75, Sanyo Chemical Industries, Ltd.) and 1.2 ml of ethyl acetate were added to a vessel. Lactic acid was also added thereto so that the adhesive layer should contain lactic acid in 5%, and the mixture was mixed. To the mixture, Compound A was added so that the adhesive layer should contain Compound A in 10%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 56

4.19 g of an acrylic adhesive (POLYTHICK 410-SA, Sanyo Chemical Industries, Ltd.), 8.0 mg of a curing agent (POLYTHICK SC-75, Sanyo Chemical Industries, Ltd.) and 1.2 ml of ethyl acetate were added to a vessel. Lactic acid was also added thereto so that the adhesive layer should contain lactic acid in 10%, and the mixture was mixed. To the mixture, Compound A was added so that the adhesive layer should contain Compound A in 10%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 57

3.67 g of an acrylic adhesive (POLYTHICK 410-SA, Sanyo Chemical Industries, Ltd.), 7.0 mg of a curing agent (POLYTHICK SC-75, Sanyo Chemical Industries, Ltd.) and 1.2 ml of ethyl acetate were added to a vessel. Lactic acid was also added thereto so that the adhesive layer should contain lactic acid in 20%, and the mixture was mixed. To the mixture, Compound A was added so that the adhesive layer should contain Compound A in 10%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 58

3.15 g of an acrylic adhesive (POLYTHICK 410-SA, Sanyo Chemical Industries, Ltd.), 6.0 mg of a curing agent (POLYTHICK SC-75, Sanyo Chemical Industries, Ltd.) and 1.2 ml of ethyl acetate were added to a vessel. Lactic acid was also added thereto so that the adhesive layer should contain lactic acid in 30%, and the mixture was mixed. To the mixture, Compound A was added so that the adhesive layer should contain Compound A in 10%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 59

2.62 g of an acrylic adhesive (POLYTHICK 410-SA, Sanyo Chemical Industries, Ltd.), 5.0, mg of a curing agent (POLYTHICK SC-75, Sanyo Chemical Industries, Ltd.) and 1.2 ml of ethyl acetate were added to a vessel. Lactic acid was also added thereto so that the adhesive layer should contain lactic acid in 40%, and the mixture was mixed. To the mixture, Compound A was added so that the adhesive layer should contain Compound A in 10%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 60

2.10 g of an acrylic adhesive (POLYTHICK 410-SA, Sanyo Chemical Industries, Ltd.), 4.0 mg of a curing agent (POLYTHICK SC-75, Sanyo Chemical Industries, Ltd.) and 1.2 ml of ethyl acetate were added to a vessel. Lactic acid was also added thereto so that the adhesive layer should contain lactic acid in 50%, and the mixture was mixed. To the mixture, Compound A was added so that the adhesive layer should contain Compound A in 10%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Experiment 5

Using the same manner as Experiment 2, each skin permeability of the formulations of Examples 53 to 60 was tested. The results were shown in Table 6.

TABLE 6

| Permeated amount of Compound A in 24 hour permeability experiment | |
|---|---|
| Example (concentration of lactic acid) | (μg/cm$^2$/24 hours) |
| Example 53 (0.3%) | 0.404 |
| Example 54 (0.5%) | 0.499 |
| Example 55 (5%) | 1.788 |
| Example 56 (10%) | 4.546 |
| Example 57 (20%) | 9.607 |
| Example 58 (30%) | 14.411 |
| Example 59 (40%) | 20.474 |
| Example 60 (50%) | 14.549 |

All the tape preparations prepared in each Example wherein the content of a permeation enhancer: lactic acid is 0.3% to 50% exhibited an excellent skin permeability.

Example 61

3.99 g of an acrylic adhesive (Oribain BPS-4849-40, TOYO INK), 0.14 g of a curing agent (Oribain BHS-0.8515, TOYO INK) and 1.2 ml of ethyl acetate were added to a vessel. Lactic acid was also added thereto so that the adhesive layer should contain lactic acid in 10%, and the mixture was mixed. To the mixture, Compound A was added so that the adhesive layer should contain Compound A in 9%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 62

3.60 g of an acrylic adhesive (DURO-TAK 87-2194, National Starch and Chemical Co.) and 1.2 ml of ethyl acetate were added to a vessel. Lactic acid was also added thereto so that the adhesive layer should contain lactic acid in 10%, and the mixture was mixed. To the mixture, Compound A was added so that the adhesive layer should contain Compound A in 9%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Example 63

3.90 g of an acrylic adhesive (DURO-TAK 387-2516, National Starch and Chemical Co.) and 1.2 ml of ethyl acetate were added to a vessel. Lactic acid was also added thereto so that the adhesive layer should contain lactic acid in 10%, and the mixture was mixed. To the mixture, Compound A was added so that the adhesive layer should contain Compound A in 9%, and the given mixture was stirred well. The mixture was flatly laid on a support so that the thickness of the adhesive layer after dried should be about 50 μm. And then it was dried at room temperature for a week. Then, a release liner was laminated on the opposite side of the adhesive layer to the support to prepare a tape preparation.

Experiment 6

Using the same manner as Experiment 2, each skin permeability of the formulations of Examples 61 to 63 was tested. The results were shown in Table 7.

TABLE 7

Permeated amount of Compound A in 24 hour permeability experiment

| Example | ($\mu g/cm^2$/24 hours) |
| --- | --- |
| Example 61 | 5.236 |
| Example 62 | 3.632 |
| Example 63 | 3.996 |

All the tape preparations prepared in Examples 61 to 63, wherein Compound A and the permeation enhancer were set in a constant amount and the kind of the acrylic adhesive was varied, exhibited an excellent skin permeability, and further the skin permeability of Compound A was enhanced by adding a permeation enhancer even when the acrylic adhesive was varied widely.

INDUSTRIAL APPLICABILITY

The tape preparation of the present invention can make it possible to inhibit the generation of a metabolite, continuously maintain the blood concentration of blonanserin, and in addition enhance the skin permeability of blonanserin with a specific permeation enhancer. Therefore, the present invention is a practically preferable tape preparation.

The invention claimed is:

1. A tape preparation comprising an adhesive layer formed on one surface of a support, wherein the adhesive layer comprises:
    (1) 2-(4-ethyl-1-piperazinyl)-4-(4-fluorophenyl)-5,6,7,8,9,10-hexahydrocycloocta[b]pyridine (hereinafter referred to as "Compound A") or a physiologically acceptable acid addition salt thereof,
    (2) an acrylic adhesive, and
    (3) lactic acid as a first permeation enhancer in a concentration of 0.1% to about 40% by weight,
    wherein Compound A is the only active ingredient in the adhesive layer.

2. The tape preparation of claim 1 wherein the adhesive layer further comprises (4) a second permeation enhancer besides (3) lactic acid as the first permeation enhancer, and the total concentration of said first and second permeation enhancers is about 0.3% to about 40% by weight.

3. The tape preparation of claim 1 wherein Compound A is present in a concentration of about 0.1% to about 50% by weight.

4. The tape preparation of claim 1 wherein the acrylic adhesive (2) is at least one selected from the group consisting of a (co)polymer mainly containing an alkyl (meth)acrylate, and a copolymer of an alkyl (meth)acrylate and a functional monomer.

5. The tape preparation of claim 2 wherein the second permeation enhancer (4) is at least one selected from the group consisting of a saturated or unsaturated $C_{7-22}$ aliphatic alcohol, diisopropyl adipate, medium chain fatty acid triglyceride, propylene glycol, oleic acid, crotamiton, N-methyl-2-pyrrolidone, olive oil, soybean oil, myristic acid, glycerin, macrogol 200, squalane, liquid paraffin, polyoxyethylene (160)polyoxypropylene(40)glycol, polyoxyethylene-nonylphenyl ether, lauromacrogol, α-monoisostearyl glyceryl ether, polyoxyethylene hydrogenated castor oil 10, isopropyl myristate, diethyl sebacate, sorbitan sesquioleate, polyoxyl 40 stearate, polyethylene glycol monolaurate, cetanol.polyethyleneglycol monostearate mixed wax, liquid lanolin, acetic acid, cetyl lactate, oleyl oleate, cetyl 2-ethylhexanoate, n-butyl acetate, l-menthol, methylisobutyl ketone and triacetin.

6. The tape preparation of claim 1 whose target disease is schizophrenia.

7. The tape preparation of claim 1 wherein Compound A is present in a concentration of about 0.5% to about 30% by weight.

8. A tape preparation comprising an adhesive layer formed on one surface of a support, wherein the adhesive layer comprises:
    (1) 2-(4-ethyl-1-piperazinyl)-4-(4-fluorophenyl)-5,6,7,8,9,10-hexahydrocycloocta[b]pyridine (hereinafter referred to as "Compound A") or a physiologically acceptable acid addition salt thereof,
    (2) an acrylic adhesive,
    (3) lactic acid as a first permeation enhancer, and
    (4) a second permeation enhancer,
    wherein the total concentration of said first and second permeation enhancers is about 0.01% to about 50% by weight, and
    wherein Compound A is the only active ingredient in the adhesive layer.

* * * * *